United States Patent [19] [11] 4,046,804
Cohen et al. [45] Sept. 6, 1977

[54] PROCESS FOR PREPARING A NOVEL BENZYLAMINE HYDRATE

[75] Inventors: Edward M. Cohen, Norristown; Earl R. Oberholtzer, North Wales, both of Pa.

[73] Assignee: Merck & Co., Inc., Rahway, N.J.

[21] Appl. No.: 728,675

[22] Filed: Oct. 1, 1976

Related U.S. Application Data

[62] Division of Ser. No. 596,942, July 18, 1975.

[51] Int. Cl.² .............................................. C07C 143/10
[52] U.S. Cl. ................................ 260/501.21; 424/316
[58] Field of Search .................................... 260/501.21

[56] References Cited

U.S. PATENT DOCUMENTS 3,812,177  5/1974  Engelhardt et al. ............ 260/501.21

Primary Examiner—James O. Thomas
Assistant Examiner—Nicky Chan
Attorney, Agent, or Firm—Daniel T. Szura; J. Jerome Behan

[57] ABSTRACT $\alpha,\alpha$-Dimethyl-4-($\alpha,\alpha,\beta,\beta$-tetrafluorophenethyl)benzylamine isethionate monohydrate and processes for its preparation are disclosed.

3 Claims, No Drawings

PROCESS FOR PREPARING A NOVEL BENZYLAMINE HYDRATE

This is a division of copending U.S. application Ser. No. 596,942, filed July 18, 1975.

BACKGROUND OF THE INVENTION

The non-toxic pharmaceutically acceptable salts of certain tetrafluorophenethyl benzylamines are active anti-arrhythmic agents. A preferred agent of this class is α,α-dimethyl-4-(α,α,β,β-tetrafluorophenethyl)benzylamine isethionate. These benzylamines, their preparation and utility are disclosed in U.S. Pat. No. 3,812,177 issued May 21, 1974.

A novel monohydrate of α,α-dimethyl-4-(α,α,β,β-tetrafluorophenethyl)benzylamine isethionate has been discovered. This monohydrate can be readily converted to the anhydrous form for utilization in dosage forms. The process for preparing the monohydrate also offers a means of recrystallizing and/or purifying the isethionate salt from aqueous solution.

SUMMARY OF THE INVENTION

α,α-Dimethyl-4-(α,α,β,β-tetrafluorophenethyl)benzylamine isethionate monohydrate and processes for its preparation.

DESCRIPTION OF THE PREFERRED EMBODIMENTS

A preferred embodiment of the present invention is α,α,-dimethyl-4-(α,α,β,β-tetrafluorophenethyl)benzylamine isethionate monohydrate, represented by the formula

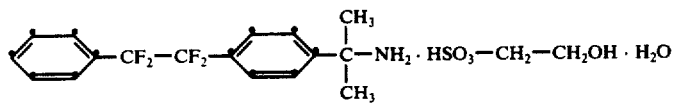

The compound (I) occurs in crystalline form. It is readily converted to the anhydrous moiety by heating in air at about 60° C. This anhydrous salt is especially suitable for preparing pharmaceutical dosage forms useful for treating arrhythmia.

Another embodiment of the present invention is the process for preparing the monohydrate of Formula I. The monohydrate is prepared from an aqueous solution containing less than 10% and preferably about 5% by weight of α,α-dimethyl-4-(α,α,β,β-tetrafluorophenethyl)benzylamine isethionate using (1) a freeze/thaw cycle or (2) cooling at about 5° C. and seeding with Formula I compound. The thawing step in process (1) is preferably carried out at about 5° C., that is 4°–6° C., and preferably at 5° C.

The solution concentrations is important since the monohydrate is not obtained from solutions containing 10% by weight, or more, of the isethionate.

The monohydrate precipitates, or is seeded, out of the solution as a crystalline material.

The preparation of the monohydrate from aqueous solution followed by removal of the water of hydration by heating at suitable temperatures also provides a convenient and improved system for recrystallizing and/or purifying the non-hydrated isethionate without using any solvent except water.

The following examples illustrate the preparation of the monohydrate of Formula I. The non-hydrated isethionate can be prepared as described in U.S. Pat. No. 3,812,177.

EXAMPLE 1

An aqueous solution containing 5.6% by weight of α,α-dimethyl-4-(α,α,β,β-tetrafluorophenethyl)benzylamine isethionate was frozen. The frozen solution was then allowed to thaw at 5° C. A crystalline precipitate formed. This precipitate was separated from the solution and identified as α,α-dimethyl-4-(α,α,β,β-tetrafluorophenethyl)benzylamine isethionate monohydrate by infra-red, ultraviolet, X-ray and loss-on-drying analyses.

EXAMPLE 2

An aqueous solution containing 50 milligrams/milliliter of α,α,-dimethyl-4-(α,α,β,β-tetrafluorophenethyl)benzylamine isethionate is prepared. This solution is stored at 5° C. until temperature equilibrium is reached. At that time, seed crystals (about 2 milligrams) of the hydrate of Example 1 are added. After standing for 24 hours, the crystalline α,α-dimethyl-4-(α,α,β,β-tetrafluorophenethyl)benzylamine isethionate monohydrate which precipitates, is separated from the solution.

What is claimed is:

1. A process for preparing α,α-dimethyl-4-(α,α,β,β-tetrafluorophenethyl)benzylamine isethionate monohydrate which comprises
   a. preparing an aqueous solution containing less than 10% by weight of α,α-dimethyl-4-(α,α,β,β-tetrafluorophenethyl)benzylamine isethionate,
   b. freezing said solution,
   c. thawing said frozen solution at a temperature of about 5° C. and
   d. separating therefrom α,α-dimethyl-4-(α,α,β,β-tetrafluorophenethyl)benzylamine isethionate monohydrate which precipitates.

2. The process of claim 1 wherein said solution contains about 5% by weight of α,α-dimethyl-4-(α,α,β,β-tetrafluorophenethyl)benzylamine isethionate.

3. The process of claim 1 wherein said solution contains 5.6% by weight of α,α-dimethyl-4-(α,α,β,β-tetrafluorophenethyl)benzylamine isethionate and said temperature is 5° C.